(12) United States Patent
Danielsson et al.

(10) Patent No.: US 6,542,572 B2
(45) Date of Patent: Apr. 1, 2003

(54) COMPUTED TOMOGRAPHY METHOD INVOLVING A HELICAL RELATIVE MOTION

(75) Inventors: Per-Erik Danielsson, Linkoeping (SE); Henrik Valdemar Turbell, Linkoeping (SE)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 10/015,840

(22) Filed: Nov. 30, 2001

(65) Prior Publication Data

US 2002/0113215 A1 Aug. 22, 2002

(30) Foreign Application Priority Data

Dec. 7, 2000 (DE) .......................... 100 61 120

(51) Int. Cl.$^7$ ................................ A61B 6/03
(52) U.S. Cl. .......................... 378/15; 378/901
(58) Field of Search ..................... 378/4, 8, 15, 901

(56) References Cited

U.S. PATENT DOCUMENTS 6,072,851 A * 6/2000 Sivers ....................... 378/15

OTHER PUBLICATIONS

Henrik Turbell, Pre–Erik Danielsson, "International Journal of Imaging Systems and Technology" vol. 11, 2000, pp. 91–100 "Helical Cone–Beam Tomography".

Turbell et al., "The PI_FAST Method for Approximate Helical Cone–Beam Reconstruction," Sixth International Conference On Fully Three–Dimensional Image Reconstruction In Radiology And Nuclear Medicine, 'Online! Oct. 31, 2001, URL:http://cfi.lbl.gov/3D–2001/abstracts/05–3.pdf "gefunden am Mar. 2, 2002.

* cited by examiner

*Primary Examiner*—David V. Bruce
(74) *Attorney, Agent, or Firm*—John Vodopia

(57) ABSTRACT

The invention relates to a computed tomography method in which the summing operation required for filtered back-projection is performed in two steps, filtering being performed only after the first summing step. This method is preferably performed for the points on a surface, which is defined by parallel rays, which are situated in parallel planes and link oppositely situated segments of the helix.

8 Claims, 7 Drawing Sheets

COMPUTED TOMOGRAPHY METHOD INVOLVING A HELICAL RELATIVE MOTION

Figure 1:
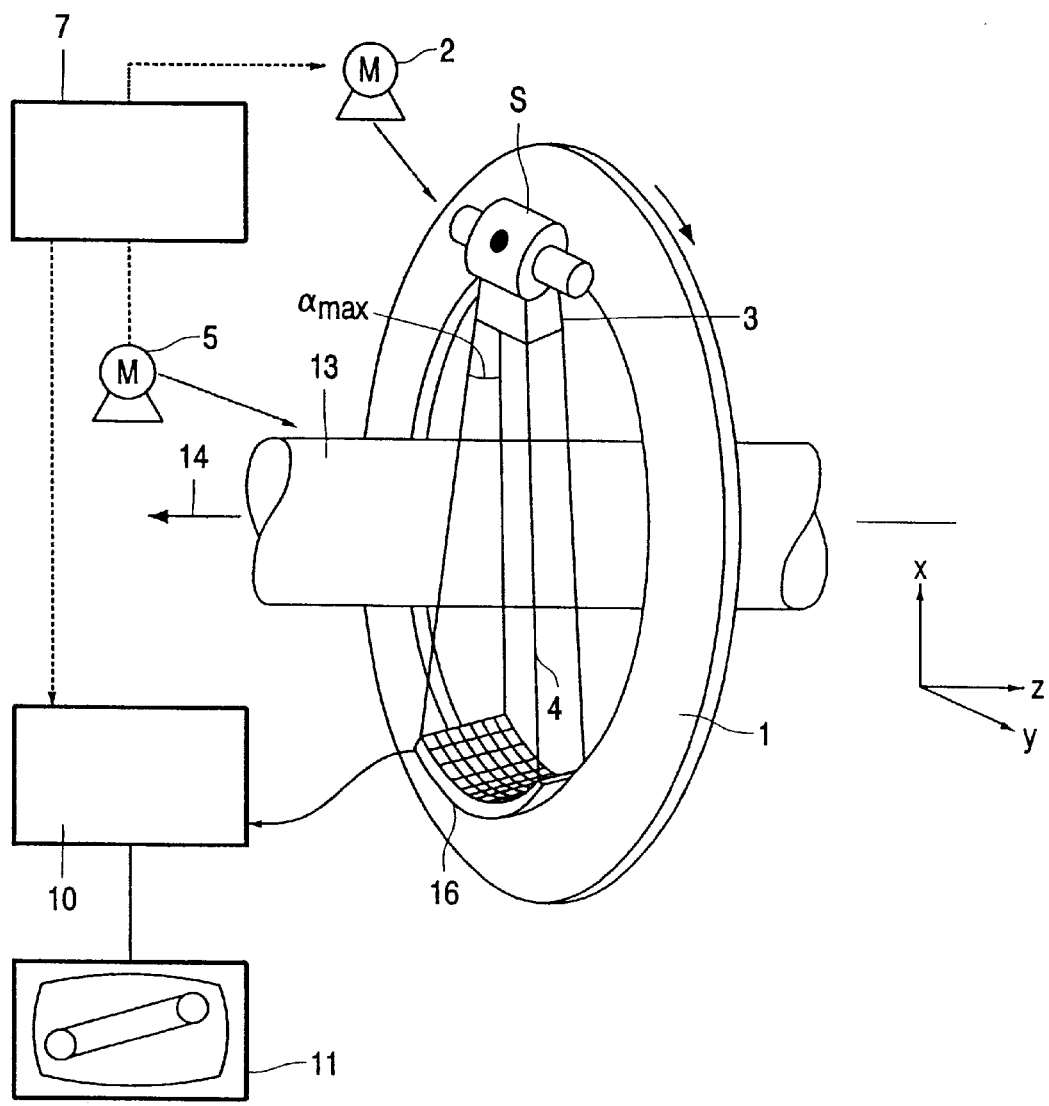

The invention relates to a computed tomography method wherein a radiation source which emits a conical radiation beam performs a relative motion in the form of a helix relative to an examination zone. The invention also relates to a computed tomography apparatus and to a computer program for carrying out such a method.

A computed tomography method of this kind is known from PCT/IB 99/00027 (PHQ 98-020). Therein, a CT image is reconstructed from the acquired measured values by applying the filtered backprojection method wherein the measured values are subjected to one-dimensional ramp-like filtering after a so-called parallel rebinning operation. The filter data associated with rays having passed through a given point in the examination zone is subsequently summed; this yields the attenuation coefficient for the rays of the radiation beam in the relevant point.

Despite the attractive quality of the CT (CT=Computed Tomography) image thus formed, it may still contain image artefacts, notably when the conical radiation beam has a large angle of aperture in the direction perpendicular to the axis of rotation and parallel thereto.

It is an object of the present invention to realize a further enhancement of the image quality offered by a method of the kind set forth. This object is achieved by means of a computed tomography method which includes the steps of:
(a) generating a conical radiation beam which contains a plurality of rays that emanate from a radiation source and traverse an examination zone or an object present therein,
(b) generating a relative motion between the radiation source on the one side and the examination zone or the object on the other side, which relative motion includes a rotation about an axis of rotation and a displacement relative to the axis of rotation and is shaped as a helix,
(c) acquiring measured values, using a detector unit, which are dependent on the attenuation of the rays in the examination zone during the relative motion,
(d) calculating link values by summing the measured values along links of a network in a three-dimensional parameter space describing the position and orientation of the rays,
(e) filtering the link values in order to produce filter data for links that are associated with rays that pass through a given surface of the examination zone,
(f) calculating the attenuation of the radiation in pixels on the surface by summing the filter data of links which approximate the trajectory that is defined in the parameter space by the rays that pass through the relevant pixel,
(g) repeating at least the steps e) and f) for other surfaces that are mutually offset in the direction of the axis of rotation.

The invention is based on the recognition of the fact that the artefacts occurring in the known method are due to the fact that the assembly of measured values subjected to a common (one-dimensional and ramp-like) filter operation changes from one filter operation to another. In accordance with the invention, however, the various filter operations are performed only on measured values that are associated with rays that pass at least approximately through one and the same surface in the examination zone.

Limiting the filter operations to these measured values is possible because a two-stage summing operation is performed in conformity with the characteristics d) and f) and because the filter operation in conformity with the characteristic e) is inserted between these two steps.

Claim 2 discloses a preferred version of the invention. All rays passing through the surface defined in claim 2 are situated in planes which extend parallel to the axis of rotation and together define an angular range of exactly 180°. Therefore, the attenuation in this surface can be reconstructed without utilizing redundant measured data. For all other surfaces it would be necessary to take into account rays from a larger angular range.

It is to be noted that a publication in the name of the inventor in the magazine "International Journal of Imaging Systems and Technology", Vol. 11, 2000 (pp. 91–100) discloses a method for filtered backprojection in which the one-dimensional filtering (preceding the backprojection) involves the measured values of rays that pass through a plane that contains the axis of rotation along inclined lines. These lines approximate the projection of a surface which is referred to as Pi-surface (being identical to the surface defined in claim 2) onto the plane. However, the projection is line-shaped for a few projection directions only. Therefore, optimum image quality is not achieved when the attenuation is reconstructed each time two-dimensionally for a series of such surfaces. Moreover, the filtering and the backprojection therein take place in the customary order, while in the present invention these two steps are interleaved comprising the above three steps d), e), and f).

The further version disclosed in claim 3 is advantageous notably when the detector unit has comparatively large dimensions in the direction of the axis of rotation. It can be dispensed with in the case of smaller dimensions, because the cosine function then suitably approximates the value 1 for all rays.

When the attenuation values are acquired at the grid points of a regular Cartesian grid in conformity with claim 4, CT images of arbitrary surfaces in the examination zone can be simply formed at a later stage.

Seemingly, the larger the angular range wherefrom measured values are acquired for the calculation of link values before the filtering, the more specifically are these data related to one Pi-surface only. On the other hand, a requirement for not filtering original projection data in the customary way is that the links are straight line segments. The larger the angular range, the less accurate is the piece-wise linear approximation of pixel-trajectories in measurement space. A suitable compromise between these contradictory requirements is offered by the version disclosed in claim 5.

The rays are advantageously subjected to so-called parallel rebinning in conformity with claim 6.

Claim 7 describes a computed tomography apparatus which is suitable for carrying out the method in accordance with the invention and claim 8 discloses a computer program for executing the reconstruction method in accordance with the invention.

Figure 2:
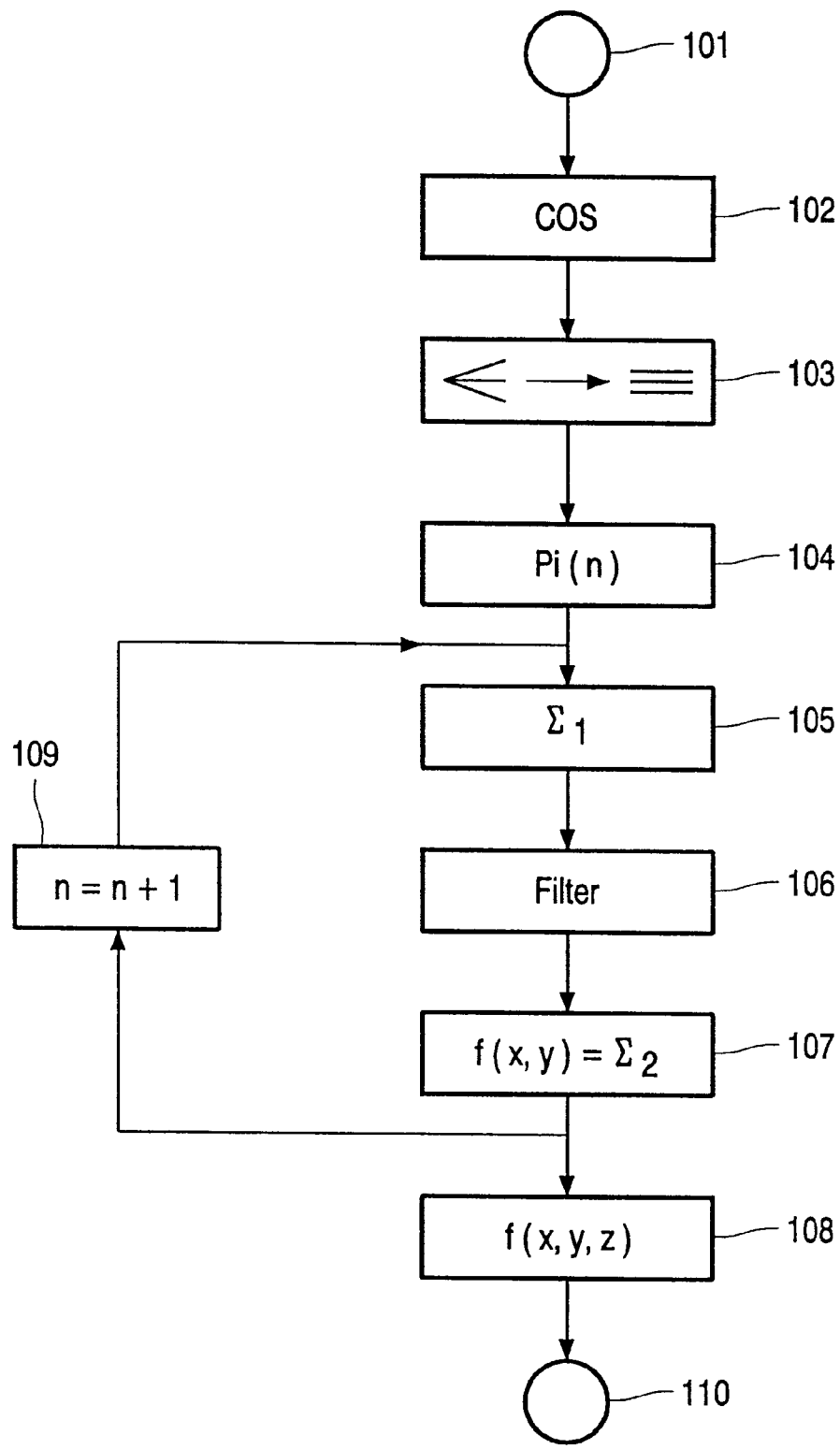
Figure 3:
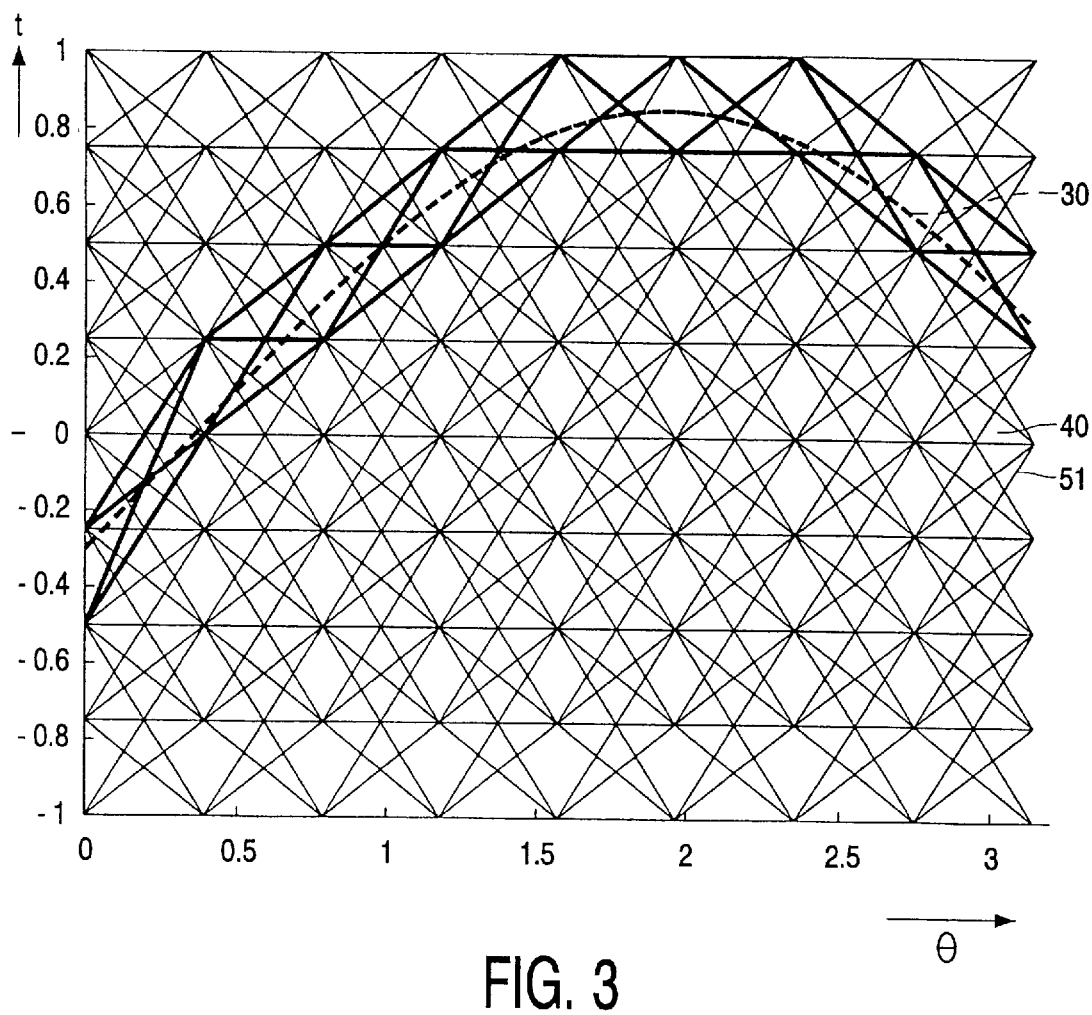
Figure 4:
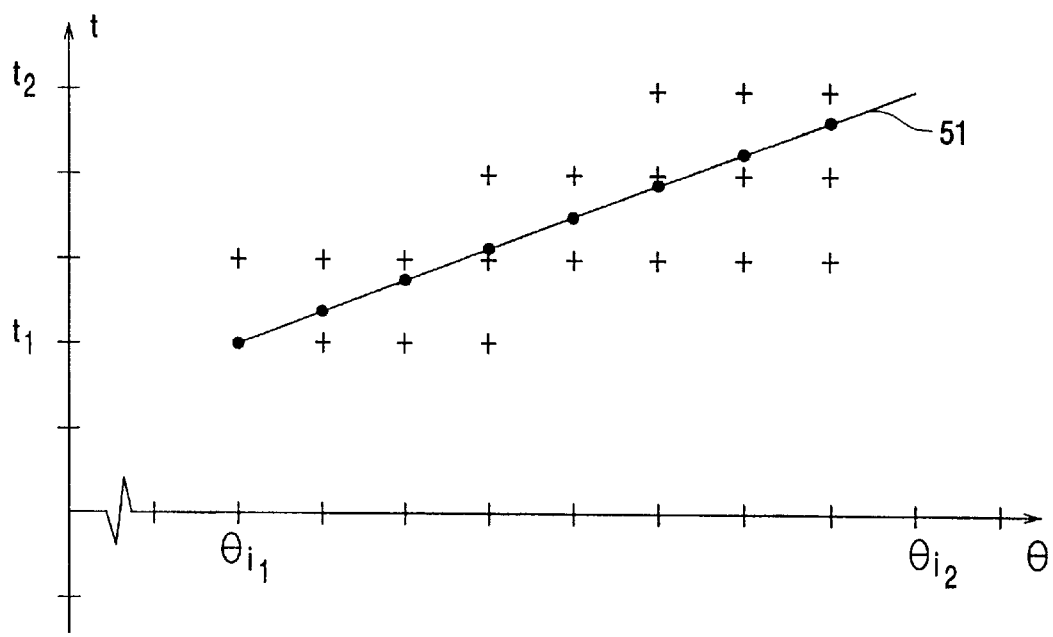
Figure 5:
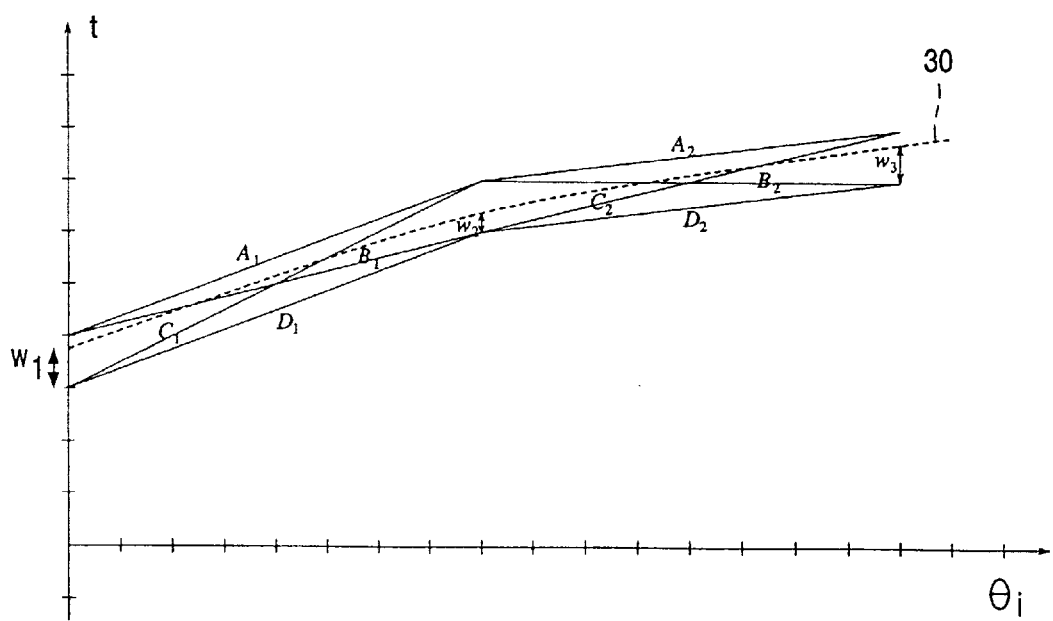
Figure 6:
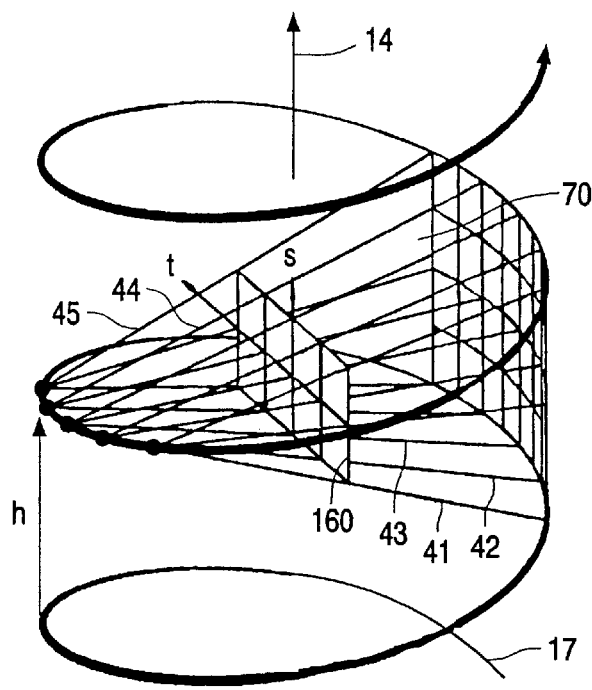
Figure 7:
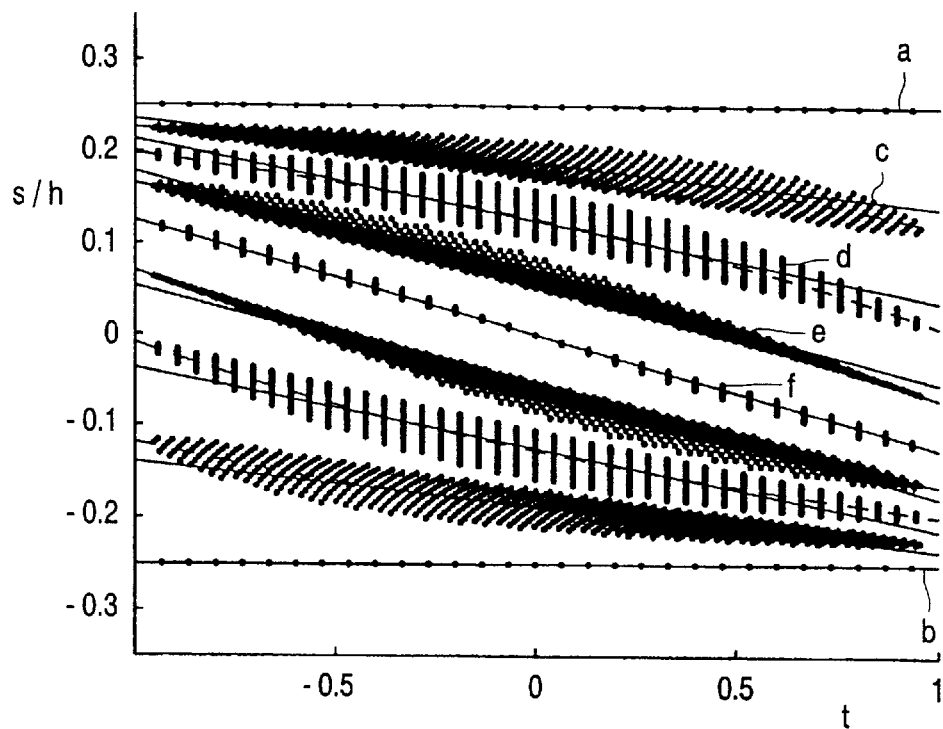
Figure 8:
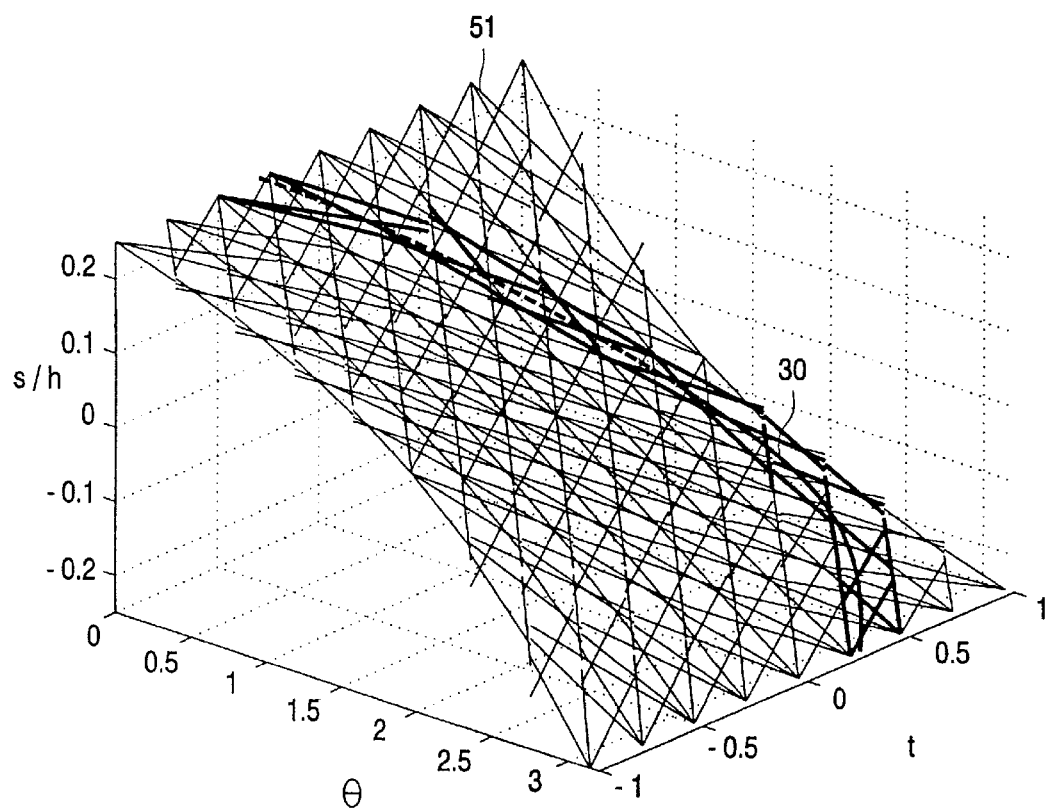
Figure 9:
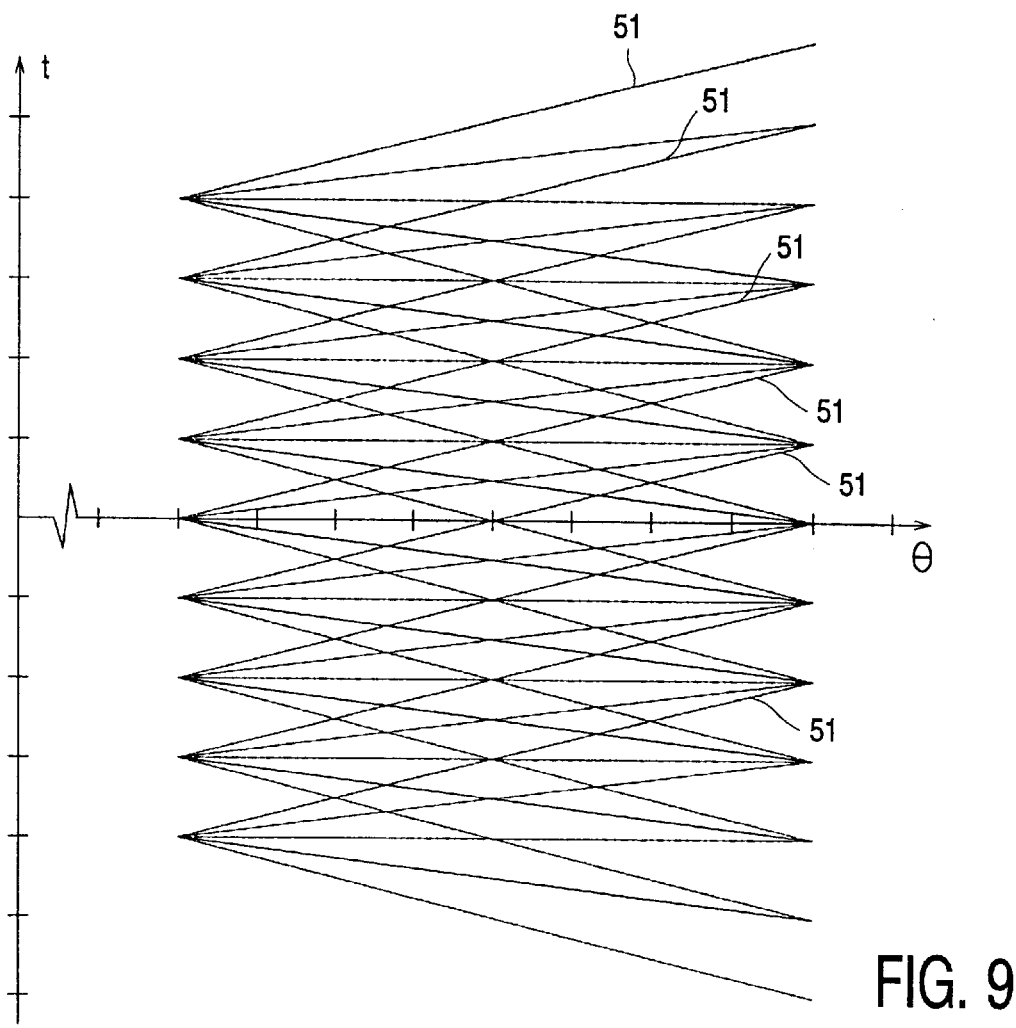
Figure 10:
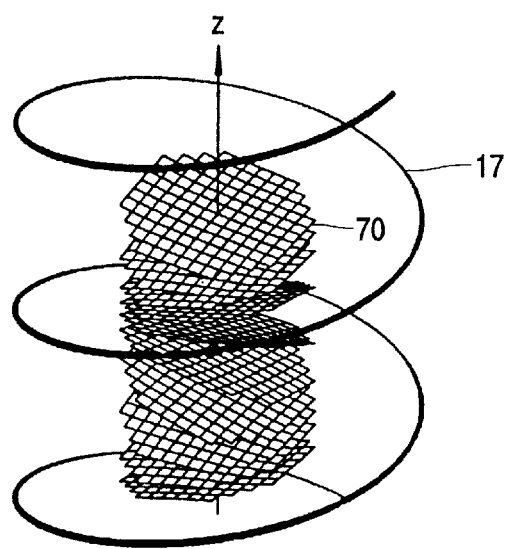

The invention will be described in detail hereinafter with reference to the drawings: Therein:

FIG. 1 shows a computed tomography apparatus which is suitable for carrying out the method in accordance with the invention, FIG. 2 shows a flow chart illustrating the method in accordance with the invention, FIG. 3 shows a two-dimensional parameter space which describes the position and the orientation of the rays, FIG. 4 shows the position of a link in such a parameter space, FIG. 5 shows a plurality of such links which approximate a segment of the trajectory connecting the rays that pass through a pixel, FIG. 6 shows the geometrical conditions underlying the invention, FIG. 7 shows the projection of various pixels on a plane containing the axis of rotation, FIG. 8 shows a three-dimensional parameter space with a network of links, FIG. 9 shows the links that are subjected to a common filter operation, and FIG. 10 shows the position of the reconstructed surfaces relative to the helical path described by the radiation source.

The computed tomography apparatus shown in FIG. 1 includes a scanning unit in the form of a gantry 1 which is capable of rotation about an axis of rotation 14. To this end, the gantry is driven at a preferably constant but adjustable angular speed by a motor 2. A radiation source S, for example an X-ray source, is mounted on the gantry 1. The source is provided with a collimator device 3 which forms a conical radiation beam 4 from the radiation produced by the radiation source S, that is, a radiation beam which has a finite dimension other than zero in a plane perpendicular to the axis of rotation as well as in the direction of the axis of rotation.

The radiation beam 4 passes through an examination zone 13 in which a patient may be accommodated on a patient table (both not being shown). The examination zone 13 is shaped as a cylinder. After having traversed the cylinder, the X-ray beam 4 is incident on a two-dimensional detector unit 16 which is connected to the gantry 1 and comprises a number of detector elements which are arranged in the form of a matrix. Each detector element can deliver a measured value for a ray of the radiation beam 4 in each position of the radiation source. The detector elements are arranged in rows and columns. The detector columns extend parallel to the axis of rotation. The detector rows may be situated in planes extending perpendicularly to the axis of rotation, for example on an arc of a circle around the radiation source S. The detector rows usually contain a number of detector elements (for example, 1000) which is considerably larger than the number of detector elements in the detector columns (for example, 16).

The angle of aperture of the radiation beam 4, denoted by the reference $\alpha_{max}$ (the angle of aperture is defined as the angle enclosed by a ray of the beam 4 which is situated at the edge of the radiation beam 4 relative to a plane defined by the radiation source and the axis of rotation 14), then determines the diameter of the cylinder within which the object to be examined must be situated during the acquisition of the measured values. The object to be examined, or the patient table, can also be displaced parallel to the axis of rotation 14 by means of a motor 5. The speed of this displacement is preferably constant, but adjustable. When the two motors 5 and 2 are simultaneously active, the radiation source S and the detector unit 16 perform a helical scanning motion.

The measured values acquired by the detector unit 16 on the rotating gantry 1 is applied to an image processing computer 10 which is usually situated in a fixed point in space and is connected to the detector unit via a data loop (not shown) which operates in a contactless manner. The image processing computer 10 is capable of performing various image processing operations. It is inter alia capable of reconstructing the attenuation of the X-rays in the examination zone 13 from the acquired measured values, thus producing a 3D data set.

The invention will be described in detail hereinafter with reference to the flow chart that is shown in FIG. 2. After the initialization (block 101), the motors 2 and 5 are simultaneously activated so that the radiation source S moves along a helical path relative to the object to be examined. In the step 102 the detector unit 16 acquires measured values which, possibly after smoothing and logarithmation, correspond to the line integrals of the attenuation along the rays along which they have been measured. In a three-dimensional ($\beta,\gamma,s$) parameter space such measured values $p(\beta,\gamma,s)$, or the associated rays, are characterized by the direction $\beta$ of a perpendicular from the relevant radiation source position to the axis of rotation 14 (where $\beta$ may become larger than $2\pi$ after more than one revolution), by the angle $\gamma$ that is enclosed by the ray associated with the relevant measured value relative to a plane that contains said perpendicular, and by the height co-ordinate s of the ray (in a plane which is perpendicular to the perpendicular and contains the axis of rotation). Each ray is characterized by a point in this three-dimensional parameter space.

If necessary, during this step all measured values can be weighted with the cosine of the angle enclosed by the associated ray relative to a plane extending perpendicularly to the axis of rotation. However, when the cosine has substantially the value 1 for all rays, the step can also be omitted; it becomes necessary when the dimensions of the detector 16 are no longer negligibly small in comparison with the distance from the radiation source.

During the next step (103) a so-called parallel rebinning operation can be performed in conformity with the relation $$p(\beta, \gamma, s) = p\left(\theta - \arcsin\frac{t}{R}, \arcsin\frac{t}{R}, s\right) \to p^P(\theta, t, s) \quad (1)$$

The new set of measured values $p^P(\theta, t,s)$ thus produced is characterized by the (projection) direction $\theta$ of the ray that is associated with the relevant measured value in a plane perpendicular to the axis of rotation 14, by the distance t between this ray and the axis of rotation 14, and by the previously explained co-ordinate s. Even though the new measured values thus obtained by resorting and re-interpolation are equivalent to the original measured values $p(\beta,\gamma,s)$, they are also referred to hereinafter as projection values for the purpose of distinction and are characterized by the superscript P. The rays associated with this measured data define a regular grid in the ($\theta$, t,s) parameter space.

The reconstruction method that is known from the previously mentioned document and the reconstruction method in accordance with the invention will be described in detail hereinafter on the basis of a simplified example. The simplification is based on the assumption that the detector unit comprises only a single row of detectors so that s=0. In conformity with the known method the rebinning operation is succeeded by a filtering step in which all measured values having the same projection angle $\theta$ and a different t are subjected to a common filter operation.

The filtered data is backprojected into space only after that; contributions from all rays having passed through the relevant point are then summed so as to calculate the attenuation value for a point in the examination zone. For this step reference is made to FIG. 3 which shows the two-dimensional ($\theta$,t) parameter space with the projection angle $\theta$ as the abscissa and the co-ordinate t. Heavy, dashed lines in the parameter space denote a trajectory 30 which interconnects, over a projection angle range $\theta$ of from 0 to $\pi$, the rays that have passed through the relevant point. These rays usually do not coincide with one of the grid points in the ($\theta$,t) parameter space at which the projection values $p^P$ are situated. Therefore, the values to be used for the backprojection must be determined by interpolation. Because of the sine-like course of the trajectory 30, the rendition of FIG. 3 often is also referred to as a sinogram.

The invention takes a different approach. The summing operation performed during the backprojection throughout the projection angle range of from 0 to θ is carried out in two sub-steps and the filter step is not carried out before the backprojection but between the two sub-steps of the backprojection. To this end, a network 40 is formed in the parameter space; the nodes of this network are situated at a distance in the θ direction and the t direction which is substantially larger than the distance of the grid points of the cubic grid at which projection values are defined. Neighboring columns of nodes are interconnected by links 51. Some of these links 51 have a slope which equals at least the largest slope of a trajectory 30 in the sinogram. Any trajectory can thus be approximated by a set of links. FIG. 3 shows the links approximating the trajectory 30 in heavy lines.

The first partial summing operation is performed by calculating link values by calculating and summing the projection values along each of the links of the network. This will be illustrated with reference to FIG. 4 which shows a part of the sinogram of FIG. 3 as well as a single link 51 which links the points ($\theta_{i1}$, $t_1$ and $\theta_{i2}$, $t_2$). Some of the grid points at which the values $p^P$ are defined are denoted by crosses in FIG. 4. As is shown in FIG. 4, the grid points do not coincide with the points on the link that are obtained for each projection angle increment. The end points of the link 51 need not necessarily coincide either with a grid point. The calculation of the link value $I(\theta_{i1}, t_1; \theta_{i2}, t_2)$ for the link 51 between the points ($\theta_{i1}$, $t_1$) and ($\theta_{i2}$, $t_2$) is in conformity with the equation:

$$I(\theta_{i_1}, t_1; \theta_{i_2}, t_2) = \sum_{i=i_1}^{i_2-1} p^P\left(\theta_1, t_1 + \frac{i-i_1}{i_2-i_1}(t_2-t_1)\right) \quad (2)$$

The filter step that is yet to be described and is subsequently executed produces filtered data from the link values. During the second summing step in conformity with FIG. 5 the filter data of the links $A_1 \ldots D_1$ and $A_2 \ldots D_2$ which approximate the trajectory 30 are summed. FIG. 5 shows only a part of the trajectory and the links. The attenuation value f(x,y) for the point (x,y), being referred to hereinafter as a pixel and associated with the trajectory 30, is calculated in conformity with the relation:

$$f(x, y) = \qquad (3)$$
$$\sum_{j=1}^{k} (w_j(w_{j+1}A_j + (1-w_{j+1})B_j) + (1-w_j)(w_{j+1}C_j + (1-w_{j+1})D_j))$$

Therein, $A_j, B_j \ldots D_j$ are filtered data for the links whereby the trajectory 30 is approximated, and k is the number of the projection intervals into which the sinogram is subdivided by the network 40. The values $w_j$ and $w_{j+1}$ are weighting factors that are dependent on the distance between the links and the trajectory 30 and whose meaning becomes apparent from FIG. 5. The number k of projection intervals varies inversely proportionally to the length of the projection intervals. Large k values correspond to a fine-meshed network and a suitable approximation of the trajectories by the links; however, they also require a major calculation effort. A suitable compromise between accuracy and calculation effort is offered by the relation: $k \approx \sqrt{N_\theta}$. Therein, $N_\theta$ is the number of projection angles which are regularly distributed over 180° and for which the projection values are defined in the three-dimensional parameter space.

Because the individual links can also be used for the approximation of the trajectories by other trajectories, the associated filter data, acquired once, are used a number of times, thus reducing the necessary calculation effort.

This method will be described in detail hereinafter for a three-dimensional data set, although in the three-dimensional case there is no surface that is accentuated in one way or another by the measurement as in the two-dimensional case of FIG. 3. Nevertheless, in the step 104 a surface is given for the pixels of which the attenuation of the radiation is to be reconstructed.

In this respect reference is made to FIG. 6 which shows the helical trajectory 17 of the radiation source relative to the examination zone, it being assumed that the radiation source moves from the bottom upwards. Furthermore, for a given projection angle there are shown a few fan beams 41, 42 . . . 45 which traverse the examination zone (not shown) in planes that are parallel to one another and parallel to the axis of rotation 14. In this respect it is assumed that the upper and the lower edge rays puncture the oppositely situated segments of the helix 17. When the detector unit is constructed in such a manner that measured values are acquired only for rays in the area between neighboring turns of the helix (or when only the measured values of these rays are evaluated), it is ensured (as is known from the cited document) that each point in the examination zone is irradiated from a projection angle range of exactly 180°.

The drawing also shows a rectangular surface 180 which contains the axis of rotation 14 and extends perpendicularly to the projection direction. The upper and the lower side of the rectangle are coincident with the upper edge rays and the lower edge rays of the parallel fan beams. The left-hand side and the right-hand side are defined by the periphery of the examination zone 13 (see FIG. 1).

Because all rays thus extend through the rectangle 180 for a given position direction, this rectangle will also be referred to as the detector window hereinafter. For other projection directions the position and orientation in space of this detector window change to the same extent as the fan beams passing therethrough. Assuming that the radiation source moves upwards along the helix 17, all points in the examination zone are first projected onto the upper edge of the detector window whereas they pass the lower edge after a change of the projection angle of 180°. The rays passing the upper edge of the detector window 6 in the rendition of FIG. 6, for example the rays 44 and 45, pass through the lower edge of the detector window 160 (which has then been shifted upwards in conformity with its height) after an increase of the projection direction by 180°.

In the step 104 this surface 70, being formed by rays which interconnect oppositely situated segments of the helix and extend in parallel planes, is preselected. This (non-flat) surface is also referred to as the Pi-surface in literature, because in the (θ, t,s) parameter space all projection values $p^P$, associated with rays passing through this surface or are situated therein, lie within a projection angle range of exactly 180°.

Only rays that are situated in this surface or pass through this surface are subjected to a common filter operation and initially a two-dimensional reconstruction of the attenuation is performed only for this surface. Another surface could also be selected, for example a flat surface. In that case, however, it would be necessary to take into account projection values $p^P$ from a projection angle range of more than 180°; this would make the filtering and reconstruction more difficult.

FIG. 7 shows the projection of the pixels in a Pi-surface onto the detector window 160 for projection directions that have been mutually offset by each time 22.50. As has already been stated, the projections of the pixels in the Pi-surface are coincident with the upper edge a upon entry in the radiation beam and with the lower edge b of the detector window 160 upon exit. The upper edge a of the detector window extends horizontally in conformity with the relation s/h=0.25, like the upper edge b in conformity with the relation s/h=−0.25, where h is the distance between two neighboring turns of the helix. For the projection directions situated therebetween the pixels of the Pi-surface 70 are no longer projected onto a straight line, but on narrow strips (c, d, e, f, etc.) which are more or less inclined relative to the horizontal straight lines a and b. The strips of neighboring projection directions may overlap.

The network 40, comprising the rays in the (θ, t,s) parameter space that pass through the Pi-surface, therefore, is no longer situated in one plane (as in the two-dimensional case) but on a curved surface. Granted, the projection of this part of the network onto a (θ, t) plane corresponds to the rendition of FIG. 3, but the nodes of this network have different s co-ordinates. A link 51, linking two rays (or nodes of the network 40) having the co-ordinates $\theta_1$, $t_1$, and $\theta_2$, $t_2$, has the co-ordinates $s_1$ and $s_2$. These two rays intersect in a pixel on the Pi-surface which has the co-ordinates x,y. The projection of this pixel (x,y) from the projection directions $\theta_1$ and $\theta_2$ onto the detector window 160 then yields the co-ordinates $s_1$ and $s_2$ associated with the link 51. FIG. 8 is a perspective view of said part of the network in the (θ, t,s) parameter space.

The link values for the links of this network are calculated in the step 105. The equation 2 then becomes:

$$I(\theta_{i_1}, t_1, \theta_{i_2}, t_2,) = \sum_{i=i_2}^{i_2-1} p^p\left(\theta_i, t_1 + \frac{i - i_1}{i_2 - i_1}(t_2 - t_i), s_1 + \frac{i - i_1}{i_2 - i_1}(s_2 - s_i)\right) \quad (4)$$

In the step 106 the link values of links associated with the part of the network that is shown in FIG. 8 are filtered in conformity with the relation:

$$\tilde{I}(\theta_{i_1}, t_1; \theta_{i_2}, t_2) = I(\theta_{i_1}, t_1, \theta_{i_2}, t_2) \hat{x} g(t) \quad (5)$$

wherein the operator $\hat{x}$ symbolizes a convolution operation and g(t) is a filter function which produces the desired ramp-like filtering because of the convolution. The equation 5 represents a one-dimensional convolution where all links that emanate from the same projection angle ($\theta_{i_1}$) and have the same slope $\Delta t = t_2 - t_1$ are subjected to a (common) filter operation. This is shown in FIG. 9 which illustrates the links that emanate from a given projection angle θ; links that have the same slope are shown in the same dashed or dotted manner therein. A filter operation involves, for example the link values of the links denoted by the reference numeral 51.

During the subsequent step 107 the filtered data of links that approximate the trajectories 30 (see FIG. 8) of the individual pixels (x,y) of the Pi-surface 70 (FIG. 6) are summed. All trajectories of pixels in this Pi-surface start from the straight lines s/h=0.25 and $\theta = \theta_i(\theta = 0$ in FIG. 8). All trajectories also end on a common line which is determined by the co-ordinates s/h=−0.25 and $\theta = \theta_i + \pi$. The calculation is performed in conformity with the equation 3, the values $A_j$ ... $D_j$ being formed by the filter data $\tilde{I}(\theta_{i_1}, t_1; \theta_{i_2}, t_2)$ calculated in the step 106 and approximating the trajectory 30.

The step 107 yields the attenuation values f(x,y) on the Pi-surface 70 given in the step 104. During the subsequent step 109, a different Pi-surface is selected; this surface deviates from the preceding Pi-surface, for example, by an increment of the projection direction and is offset in the direction of the axis of rotation 14. The steps 105 to 107 are executed again for this new Pi-surface, and are subsequently repeated for further Pi-surfaces. Finally, the attenuation values will have been acquired for a number of Pi-surfaces (shown in FIG. 10) that are mutually offset in the z direction and rotated relative to one another by increments of the projection angle.

In order to enable the representation of the spatial distribution of the attenuation f(x,y,z) in the three-dimensional zone defined by the two outer Pi-surfaces at the points of a regular Cartesian grid, for example a cubic grid, an interpolation is performed in the step 108. Because the attenuation values are already calculated for the individual Pi-surfaces for each time the same x and y co-ordinates, merely interpolation in the z direction is required. The method is subsequently terminated (step 110).

When the rebinning in conformity with the equation 1 in the step 103 is shifted to the calculation of the link values in conformity with the equation 4 in the step 104, the link values can be calculated directly from the measured values p(β,γ,s), without rebinning being necessary. The rebinning in the step 103 could thus be dispensed with.

Furthermore, in the case of a detector unit comprising detector rows that are situated in planes extending perpendicularly to the axis of rotation (or the z axis), the values s are not constant for a detector row when the detector rows are arranged, for example, on an arc of a circle around the radiation source. In that case rebinning, leading to constant values s in the three-dimensional parameter space, is not necessary either. Instead an interpolation can be performed for each of the summands in the equation 4. In order to avoid aliasing effects, the increments of the projection angle, (on which the equation 4 is based) should be reduced.

The calculation of the link values in the step 105 need not be limited to a respective surface as assumed for the method in conformity with FIG. 2. In that case, however, all link values that are necessary must be calculated before a (Pi) surface is selected and the associated link values are filtered.

What is claimed is:

1. A computed tomography method which includes the steps of
   (a) generating a conical radiation beam (4) which contains a plurality of rays that emanate from a radiation source (S) and traverse an examination zone (13) or an object present therein,
   (b) generating a relative motion between the radiation source (S) on the one side and the examination zone (13) or the object on the other side, which relative motion includes a rotation about an axis of rotation (14) and a displacement parallel to the axis of rotation and is shaped as a helix (17),
   (c) acquiring measured values, using a detector unit, which are dependent on the attenuation of the rays in the examination zone during the relative motion,
   (d) calculating link values ($I(\theta_{i_1}, t_1, \theta_{i_2}, t_2)$) by summing the measured values along links (51) of a network (40) in a three-dimensional parameter space (θ,t,s) describing the position and orientation of the rays,
   (e) filtering the link values ($I(\theta_{i_1}, t_1, \theta_{i_2}, t_2)$) in order to produce filter data ($\tilde{I}(\theta_{i_1}, t_1; \theta_{i_2}, t_2)$) for links (51) that are associated with rays that pass through a given surface (70) of the examination zone,
   (f) calculating the attenuation (f(x,y,z)) of the radiation in pixels on the surface (70) by summing the filter data ($\tilde{I}(\theta_{i_1}, t_1; \theta_{i_2}, t_2)$) of links which approximate the trajectory (30) that is defined in the parameter space (θ,t,s) by the rays that pass through the relevant pixel,
   (g) repeating at least the steps e) and f) for other surfaces that are mutually offset in the direction of the axis of rotation.

2. A computed tomography method as claimed in claim 1, characterized in that each of the surfaces (70) is defined by a respective set of rays (41 . . . 45) which are situated in planes extending parallel to the axis of rotation (14) and link oppositely situated segments of the helix (17).

3. A computed tomography method as claimed in claim 1, characterized in that the measured values are weighted with the cosine of the angle enclosed by the ray associated with the respective measured value relative to a plane extending perpendicularly to the axis of rotation.

4. A computed tomography method as claimed in claim 1, characterized in that the attenuation values (f(x,y,z)) are calculated at the grid points of a regular, three-dimensional grid, preferably a cubic grid, from the attenuation values (f(x,y)) of the pixels (x,y) on the surfaces (70).

5. A computed tomography method as claimed in claim 1, wherein measured values are taken from an angular range of $180°/N_1$ in order to calculate each link value, where $N_1$ has at least approximately the value $\sqrt{N_\theta}$ and $N_\theta$ is the number of positions of the radiation source which are distributed over an angular range of 180° and in which measured values are acquired.

6. A computed tomography method as claimed in claim 1, wherein the acquired measured values (p(β,γ,s)) are rebinned in such a manner that there is formed a new set of measured values ($p^P(\theta,t,s)$) which are associated with rays that are situated on a cartesian grid in a parameter space (θ,t,s) which is defined by the direction (θ) of the rays and their position (t,s) in a plane containing the axis of rotation (14).

7. A computed tomography apparatus for carrying out the method claimed in claim 1, which apparatus includes
- a radiation source (S) for generating a conical radiation beam (4),
- a drive device (2, 5) for producing a relative motion in the form of a helix (17) between the radiation source (S) and the examination zone,
- a detector unit (16) for the acquisition of measured values which are dependent on the attenuation of the rays in the examination zone,
- and a reconstruction unit for determining the spatial distribution of the attenuation values (f,x,y,z) in the examination zone, which unit processes the measured values as follows:
  - d) calculating link values ($I(\theta_{i1},t_1,\theta_{i2},t_2)$) by summing the measured values along links (51) of a network (40) in a three-dimensional parameter space (θ,t,s) which describes the position and the orientation of the rays,
  - e) filtering the link values ($I(\theta_{i1},t_1,\theta_{i2},t_2)$) in order to generate filter data ($\tilde{I}(\theta_{i_1},t_1;\theta_{i_2},t_2)$) for links (51) which are associated with rays passing through a given surface (70) of the examination zone,
  - f) calculating the attenuation (f(x,y,z)) of the radiation in pixels on the surface (70) by summing the filter data ($\tilde{I}(\theta_{i_1},t_1,\theta_{i_2};t_2)$) of links which approximate the trajectory (30) which is defined in the parameter space (θ,t,s) by the rays passing through the relevant pixel,
  - g) repeating at least the steps e) and f) for other surfaces which are mutually offset in the direction of the axis of rotation.

8. A computer program for processing the measured values of a computed tomography apparatus as claimed in claim 7, including the steps of:
  - d) calculating link values ($I(\theta_{i1},t_1,\theta_{i2},t_2)$) by summing the measured values along links (51) of a network (40) in a three-dimensional parameter space (θ,t,s) which describes the position and the orientation of the rays,
  - e) filtering the link values ($I(\theta_{i1},t_1,\theta_{i2},t_2)$) in order to generate filter data ($\tilde{I}(\theta_{i_1},t_1;\theta_{i_2},t_2)$) for links (51) which are associated with rays passing through a given surface (70) of the examination zone,
  - f) calculating the attenuation (f(x,y,z)) of the radiation in pixels on the surface (70) by summing the filter data ($\tilde{I}(\theta_{i_1},t_1;\theta_{i_2},t_2)$) of links which approximate the trajectory (30) which is defined in the parameter space (θ,t,s) by the rays passing through the relevant pixel,
  - g) repeating at least the steps e) and f) for other surfaces which are mutually offset in the direction of the axis of rotation.

* * * * *